United States Patent
Vitek (10) Patent No.: US 6,543,272 B1
(45) Date of Patent: Apr. 8, 2003

(54) SYSTEMS AND METHODS FOR TESTING AND CALIBRATING A FOCUSED ULTRASOUND TRANSDUCER ARRAY

(75) Inventor: Shuki Vitek, Haifa (IL)

(73) Assignee: InSightec-TxSonics Ltd. (IL)

( * ) Notice: Subject to any disclaimer, the term of this patent is extended or adjusted under 35 U.S.C. 154(b) by 0 days.

(21) Appl. No.: 09/557,050

(22) Filed: Apr. 21, 2000

(51) Int. Cl.⁷ .............................................. G01V 13/00
(52) U.S. Cl. ........................................... 73/1.83; 601/2
(58) Field of Search ............................... 73/1.82, 1.83, 73/1.86, 628; 601/2, 3, 4

(56) References Cited

U.S. PATENT DOCUMENTS

| | | |
|---|---|---|
| 4,858,597 A | 8/1989 | Kurtze et al. |
| 4,865,042 A | 9/1989 | Umemura et al. |
| 4,955,366 A * | 9/1990 | Uchiyama et al. ............. 601/4 |
| 5,247,935 A | 9/1993 | Cline et al. |
| 5,275,165 A | 1/1994 | Ettinger et al. |
| 5,291,890 A | 3/1994 | Cline et al. |
| 5,307,812 A | 5/1994 | Hardy et al. |
| 5,323,779 A | 6/1994 | Hardy et al. |
| 5,327,884 A | 7/1994 | Hardy et al. |
| 5,368,031 A | 11/1994 | Cline et al. |
| 5,368,032 A | 11/1994 | Cline et al. |
| 5,435,304 A * | 7/1995 | Oppelt et al. .................. 601/4 |
| 5,443,068 A | 8/1995 | Cline et al. |
| 5,490,840 A | 2/1996 | Uzigiris et al. |
| 5,520,188 A | 5/1996 | Hennige et al. |
| 5,526,814 A | 6/1996 | Cline et al. |
| 5,590,657 A | 1/1997 | Cain et al. |
| 5,711,300 A | 1/1998 | Schneider et al. |
| 5,769,790 A | 6/1998 | Watkins et al. |
| 5,873,845 A | 2/1999 | Cline et al. |
| 5,984,881 A * | 11/1999 | Ishibashi et al. ................ 601/2 |
| 6,182,494 B1 * | 2/2001 | Reed et al. .................. 73/1.83 |

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986 May.

Todd Fjield, et al., "The Combined Concentric–Ring and Sector–Vortex Phased Array for MRI Guided Ultrasound Surgery", IEEE Transactions on Ultrasonics, Ferroelectircs and Frequency Control, vol. 44, No. 5, pp. 1157–1167, Sep. 1997.

Nathan McDannold, et al., "MRI Evaluation of Thermal Ablation of Tumors and Focused Ultrasound", JMRI vol. 8, No. 1, pp. 91–100, Jan./Feb. 1998.

Kullervo Hynynen et al., "Principles of MR–Guided Focused Ultrasound", Chapter 25, pp. 237–243, (undated).

Harvey E. Cline, Ph.D., et al., "Focused US System for MR Imaging–Guide Tumor Ablation", Radiology vol. 194, No. 3, pp. 731–738, Mar. 1995.

* cited by examiner

Primary Examiner—John E. Chapman
(74) Attorney, Agent, or Firm—Bingham McCutchen LLP (57) ABSTRACT

Systems and methods for testing the performance of a focused ultrasound transducer array include transmitting ultrasonic energy from the transducer array towards an acoustic reflector, such as a planar air mirror, and receiving ultrasonic energy reflected off of the acoustic reflector using a sensing element. A characteristic of the reflected ultrasonic energy, such as amplitude and phase, is measured by processing circuitry, for example, by comparing the characteristic of the received ultrasonic energy to a corresponding characteristic of the transmitted ultrasonic energy to obtain an actual gain and phase shift for the received ultrasonic energy. A controller compares the actual gain and phase shift of the received ultrasonic energy to an expected gain and phase shift of the received ultrasonic energy. This information is used to calibrate the transducer array and/or to declare a system failure if the comparison indicates an error.

20 Claims, 4 Drawing Sheets

SYSTEMS AND METHODS FOR TESTING AND CALIBRATING A FOCUSED ULTRASOUND TRANSDUCER ARRAY

FIELD OF THE INVENTION

The present invention relates generally to systems and methods for performing noninvasive surgical procedures using focused ultrasound, and more particularly to systems and methods for testing and calibrating a focused ultrasound transducer array.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers driven by electric signals to produce ultrasonic energy have been suggested that may be placed external to the patient but in close proximity to the tissue to be ablated. The transducer is geometrically shaped and positioned such that the ultrasonic energy is focused at a "focal zone" corresponding to a target tissue region within the patient, heating the target tissue region until the tissue is necrosed. The transducer may be sequentially focused and activated at a number of focal zones in close proximity to one another. This series of sonications is used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or "sectors," creating a sector-vortex array. The transducer elements are generally simultaneously driven by radio frequency (RF) electrical signals at a single frequency offset in phase and amplitude. In particular, the phase and amplitude of the respective drive signals may be controlled so as to focus the emitted ultrasonic energy at a desired "focal distance," i.e., the distance from the transducer to the center of the focal zone, and/or to provide a desired energy level in the target tissue region. In addition, the phase of the respective drive signals to each of the sectors may be controlled to create a desired size and shape for the focal zone.

Transducer arrays are generally composed of numerous transducer elements that may be difficult and/or costly to fabricate and require complex drive circuitry and hardware to control and power. As part of its initial production and assembly, a focused ultrasound system is generally tested and configured, for example, to ensure that the individual transducer elements of the transducer array and/or the drive and control circuitry perform properly.

Once in operation, the system may be susceptible to degradation in performance and/or possible failure of some of the transducer elements. This degradation may be caused by normal aging processes and/or by misuse of the system. For example, the piezoelectric material forming the transducer elements may age, possibly changing their impedance or efficiency. Likewise, problems may develop in the drive circuitry during the life of the system.

Accordingly, it would be desirable to monitor and/or test the performance of a focused ultrasound transducer array to ensure its ongoing proper performance.

SUMMARY OF THE INVENTION

In accordance with a first aspect of the present invention, a method is provided for testing the performance of a focused ultrasound transducer array. An acoustic reflector is located at a position to receive ultrasonic energy transmitted by the transducer array. Ultrasonic energy is transmitted from the transducer array, the ultrasonic energy is reflected off of the reflector, and is received by a sensing element. The performance of the transducer array is then evaluated based upon the received reflected ultrasonic energy.

The reflector is preferably provided with well-defined and predictable ultrasonic reflection characteristics, and may be positioned at any location within the acoustic view of the transducer array. In one embodiment, the reflector may be a planar acoustic reflector, such as an "air mirror," placed between the acoustic fluid in which the transducer is disposed and the air above the surface of the acoustic fluid. In an alternative embodiment, the reflector may be a curved reflector or a point reflector. For a concave or "spherical cap" transducer array, a planar reflector may be located between the transducer and its geometric focal point, preferably half-way between them. In this arrangement, incidental ultrasonic energy may be reflected off of the reflector to a single point located at the center of the transducer array, i.e., to its "virtual" geometric focal point. Alternatively, if a point reflector is used, it may be located at the actual geometric focal point of the transducer array.

Thus, the reflected ultrasonic energy may be received, for example, at the virtual geometric focal point of the transducer array. The performance of the transducer array may then be quantified based on an analysis of the received ultrasonic energy. Preferably, the performance of the transducer array is quantified by exciting individual transducer elements in the transducer array and comparing one or more actual characteristics of the received ultrasonic signals, e.g., gain and/or delay, to expected characteristics of the received ultrasonic signals. The expected characteristics of the received ultrasonic signal may be obtained from an acoustic model of the testing system. In a preferred method, wherein a planar reflector is located half-way between the transducer array and the geometric focal point, the acoustic wave modeling is facilitated because the bore-sight of the reflected ultrasonic energy is incident at the point of reception, regardless of the location of the individual transducer element from which it originates. Thus, no off-bore-sight sight calculations need be made. The quantified performance of the transducer array may then be used, for example, to calibrate the transducer array and/or to declare a system failure should the performance of the transducer array be severely degraded.

In accordance with a second aspect of the present invention, a method is provided for testing a focused ultrasound transducer array having a plurality of transducer elements. An acoustic reflector, such as a planar reflector, is positioned adjacent the transducer array, and a plurality of reflected ultrasonic signals are produced by transmitting a plurality of ultrasonic signals from the plurality of transducer elements towards the acoustic reflector. The ultrasonic signals may be transmitted by exciting individual transducer elements or a set of transducer elements. As previously described, the transducer array may have a concave or spherical cap shape, and the acoustic reflector may be an "air mirror" located half-way between the transducer array and its geometric focal point.

The plurality of reflected ultrasonic signals may be received and one or more actual ultrasonic reflection characteristics, such as gain and/or delay, may obtained from each of the plurality of received ultrasonic signals. The plurality of actual ultrasonic reflection characteristics may then be compared with a plurality of expected ultrasonic reflection characteristics.

Preferably, the delay of each of the received ultrasonic signals with respect to the transmitted ultrasonic signals is determined, which may be an actual time delay (for pulsed signals) or a phase shift between the signals (for sinusoidal signals). Alternatively or in addition, the gain of each of the received ultrasonic signals may be obtained by comparing the amplitudes of the plurality of received ultrasonic signals with the corresponding amplitudes of the plurality of transmitted ultrasonic signals. This may be accomplished, for example, by comparing electrical signals produced by a sensing element representative of the received ultrasonic signals with electrical signals used to generate the transmitted ultrasonic signals, i.e., the corresponding electrical signals used to excite the transducer elements into producing the plurality of ultrasonic signals.

The actual ultrasonic reflection characteristics may be compared with a respective plurality of expected ultrasonic reflection characteristics. As previously described, the expected characteristics of the received ultrasonic energy may be obtained from an acoustic model of the testing system. The transducer array may then be calibrated, or alternatively, a system failure may be declared, based upon the ultrasonic reflection characteristic comparison.

In accordance with a third aspect of the present invention, an ultrasound system is provided that includes a focused ultrasound transducer for emitting ultrasonic energy, a passive acoustic reflector for reflecting ultrasonic energy emitted by the transducer, and an ultrasound sensing element for sensing the reflected ultrasonic energy. The transducer may, for example, be a phased transducer array used to treat abnormal tissue within a patient. In a preferred embodiment, the shape of the transducer takes the form of a spherical cap, but alternatively may take on any suitable shape that enables the focusing of ultrasonic energy. More preferably, the reflector is an air mirror located half-way between the transducer and its geometric focal point. Thus, in this embodiment, the sensing element may be located at a single point at the center of the transducer. The geometry of the reflector may be any shape that provides well-defined and predictable acoustic reflection characteristics, and may be located anywhere within the view of the transducer.

The system further includes processing circuitry coupled to the sensing element for measuring actual characteristic(s) of the received ultrasonic signals, e.g., the amplitude and/or phase. The processing circuitry may also be coupled to drive circuitry used to excite the transducer into emitting the ultrasonic energy. In this embodiment, the processing circuitry may compare the amplitude and phase of the received ultrasonic signal with the amplitude and phase of the emitted ultrasonic signal.

The system further includes a controller coupled to the processing circuitry for comparing the actual characteristic(s) of the received ultrasonic energy, e.g., the gain and/or delay (or phase shift), to expected characteristic(s) of the sensed ultrasonic energy. The controller and processing circuitry may both be a single integral component, such as a personal computer with special boards added (such as acquisition boards), or other microprocessor, or alternatively, may be separate components. The controller may then use the difference information to calibrate the emitting transducer and/or to declare a system failure if need be.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
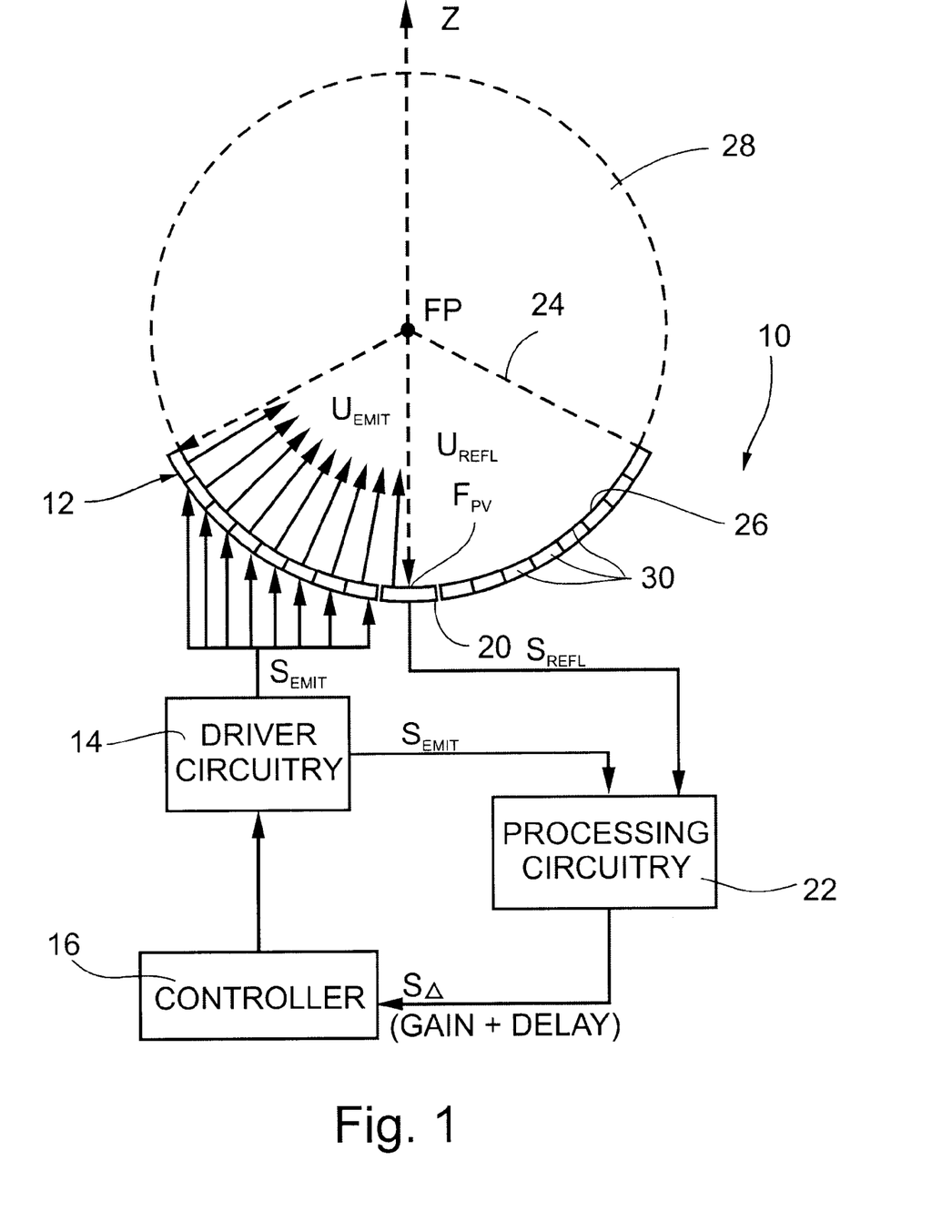
FIG. 1 is a schematic diagram of a focused ultrasound system, in accordance with the present invention.

Turning now to the drawings, FIG. 1 shows a preferred embodiment of a focused ultrasound system 10, constructed in accordance with the present invention. The system 10 may be operated to advantageously focus ultrasonic energy at a "focal zone" or desired target region in space for purposes of providing therapy to a patient, e.g., for treating abnormal tissue within the patient. To this end, the system 10 generally includes an ultrasound emitting transducer 12 for emitting ultrasonic energy $U_{EMIT}$, driver circuitry 14 for providing electrical drive signals $S_{EMIT}$ to the transducer 12, and a controller 16 for controlling the characteristics of the drive signals $S_{EMIT}$ output from the driver circuitry 14, and thus, the characteristics of the emitted ultrasonic energy $U_{EMIT}$. The transducer 12 is preferably a phased array ultrasound transducer formed from piezoelectric material, constructed as is known to those skilled in the art.

In the exemplary embodiment shown, the transducer 12 has a concave or bowl shape, preferably a "spherical cap" shape, i.e., having a substantially constant radius of curvature 24, such that the transducer 12 has an inside surface 26 defining a portion of a sphere 28. The transducer 12 has a geometric focal point FP, which, in the case of a spherical cap transducer array, is coincident with the center of the sphere.

Figure 2:
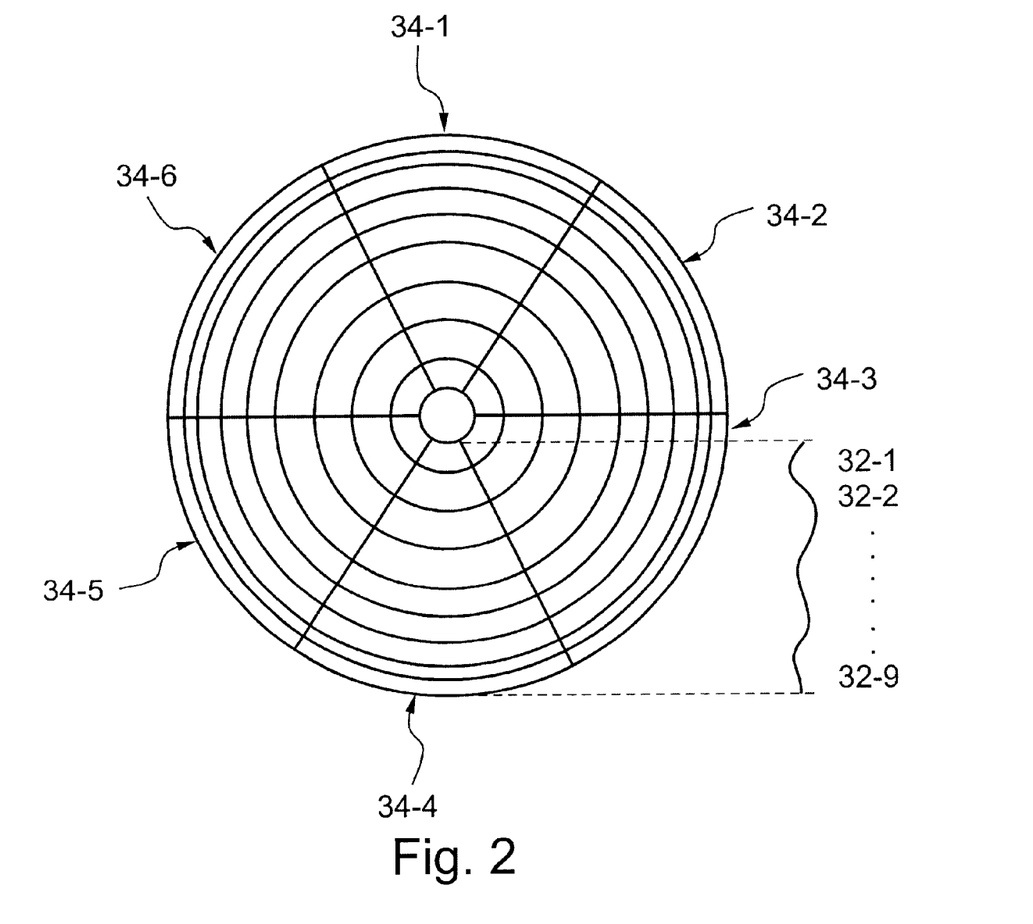
FIG. 2 is a top view of the transducer array of the focused ultrasound system of FIG. 1.

The transducer 12 includes a plurality of transducer elements 30, such as concentric rings 32-1 to 32-9, which may be formed by cutting concentric circles through a piezoelectric shell (not shown). Preferably, each of the rings 32 has substantially the same surface area, and thus, the widths of the rings 32 are progressively smaller from the innermost ring 32-1 outward to the outermost ring 32-9. Any spaces (not shown) between the rings 32 may be filled with silicone rubber and the like to substantially isolate the rings 32 from one another. Each ring 32 may also be divided circumferentially into curved elements or "sectors" 34-1 to 34-6.

In a preferred embodiment, the transducer 12 has an outer diameter of between about 8–12 cm, a radius of curvature 24 between about 8–16 cm, and includes between about ten and thirty rings 32, each of which is divided into 4–16 sectors 34, thereby providing between about 40–480 transducer elements 30. More preferably, the transducer includes twenty six rings divided into eight sectors, thereby including 208 transducer elements (not shown). The exemplary transducer 12 shown includes a total of nine rings 32 and fifty-four transducer elements 30 merely to simplify its illustration. The present invention is not limited to these numbers, and any suitable number of transducer elements 30 may be used by increasing or decreasing the number of rings 32 and/or sectors 34. The transducer 12 also preferably includes backing and matching layers (not shown) for providing the necessary acoustic characteristics for the transducer elements 30, as is known in the art.

Additional information on the construction of a phased array transducer appropriate for use with the present invention may be found, for example, in T. Fjield and K. Hynynen, "The Combined Concentric-Ring and Sector-Vortex Phased Array for MRI Guided Ultrasound Surgery," IEEE Transactions on Ultrasonics, Ferroelectrics, and Frequency Control, vol. 44, no. 5, pages 1157–1167 (September 1997), the disclosure of which is expressly incorporated herein by reference. Alternatively, a concentric-ring transducer may be provided that is not divided into circumferential sectors (not shown), such as that described in C. Cain and S. Umemura, "Concentric-Ring and Sector-Vortex Phased-Array Applicators for Ultrasound Hyperthermia," IEEE Transactions on Microwave Theory and Techniques, vol. MTT-34, no. 5, pages 542–551 (May 1986), the disclosure of which is expressly incorporated herein by reference. Alternatively, the face of the transducer may be divided into transducer elements having other shapes or geometries other than concentric rings.

Returning to FIG. 1, each of the transducer elements 30 is individually coupled to the driver circuitry 14 in a conventional manner. The driver circuitry 14 is configured to provide electrical drive signals $S_{EMIT}$ to the transducer elements 30 at a plurality of discrete frequencies, preferably at radio frequencies (RF), for example, between about 0.5 to 10 MHz, and more preferably between about 1 to 2 MHz. When drive signals $S_{EMIT}$ are provided to the transducer elements 30, the transducer 12 emits ultrasonic energy $U_{EMIT}$ from its inside surface 26.

The controller 16 is coupled to the driver circuitry 14 for controlling several aspects of the drive signals $S_{EMIT}$ generated by the driver circuitry 14, such as the frequency, phase, and/or amplitude. First, the controller 16 may control the amplitude of the drive signals $S_{EMIT}$, for example, to control the intensity of emitted ultrasonic energy $U_{EMIT}$. In addition, the controller 16 may control the phase between each of the concentric rings 32 and/or between each of the sectors 34. By shifting the phase between the concentric rings 32, the "focal distance," i.e., the distance from the transducer 12 to the center of the focal zone, may be adjusted, for example, along the z axis. Because of the phase shifting, the location of the center of the focal zone of the emitted ultrasonic energy $U_{EMIT}$ may differ from the geometric focal point FP of the transducer 12. Shifting the phase between the sectors 34 ("mode n") allows control of the size and shape of the focal zone of the transducer 12.

Of course, other methods may be employed for controlling the size, shape, and/or location of the focal zone. For example, the controller 16 may direct the drive circuitry 14 to drive respective rings 22 and/or sectors 23 in relatively short pulses that may be delayed with respect to one another in a predetermined manner, as will be appreciated by those skilled in the art. Further information on phase shifting of phased array transducers may be found in the Fjield and Cain articles referenced above, as well as in U.S. Pat. No. 4,865,042 issued to Umemura et al., the disclosure of which is expressly incorporated herein by reference.

The controller 16 also preferably controls the frequency of the drive signals $S_{EMIT}$ provided to the transducer 12. The drive signals $S_{EMIT}$ supplied to the transducer 12 at one time are all preferably provided at the same discrete frequency. This discrete frequency may be maintained during a single sonication. Alternatively, the frequency may be varied during the sonication to minimize the effects of secondary hot spots. Such a system and method is described in co-pending application Ser. No. 09/556,095, which was filed on the same date and assigned to the same assignee as the present application (hereinafter "the '159 application"). The disclosure of the '159 application and any references cited therein are expressly incorporated herein by reference.

Figure 3:
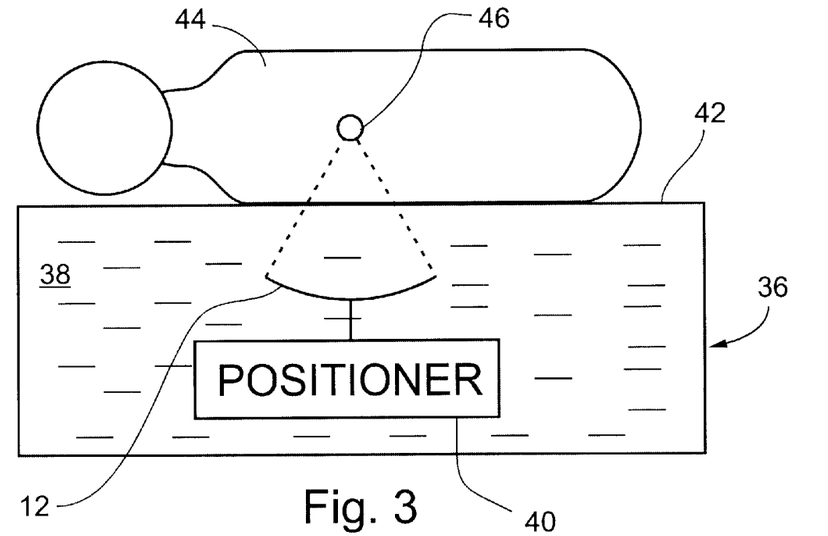
FIG. 3 is a schematic side view of a patient on a water-filled table having an ultrasound transducer array therein.

As shown in FIG. 3, the transducer 12 is preferably mounted within a fluid-filled casing, such as a table 36. The table 36 includes a chamber 38 filled with degassed water or similar acoustically transmitting fluid. The transducer 12 is preferably connected to a positioning system 40 that moves the transducer 12 within the chamber 38, and consequently adjusts the geometric focal point of the transducer 12. For example, the positioning system 40 may be configured to move the transducer 12 within the chamber 38 in any one of three orthogonal directions, e.g., horizontally forward and backward, horizontally side-to-side, and vertically. U.S. Pat. Nos. 5,247,935 issued to Cline et al. and U.S. Pat. No. 5,275,165 issued to Ettinger et al., the disclosures of which are expressly incorporated herein by reference, disclose exemplary positioning systems that may be used.

Alternatively or optionally, the positioning system 40 may pivot the transducer 12 about a fixed point within the chamber 38, i.e., to change the angle of the transducer 12 and consequently the geometric focal point FP with respect to a horizontal plane (not shown). In this positioning method, the focal distance may be controlled electronically by changing the phase and/or amplitude of the drive signals provided to the transducer 12, as described above.

The top of the table 36 includes a flexible membrane 42 that is substantially transparent to ultrasound, such as a mylar plastic or polyvinyl chloride (PVC) sheet. In addition, a flexible, fluid-filled bag (not shown) is generally provided along the top of the table that may conform easily to the contours of a patient lying on the table. In an alternative embodiment, the transducer 12 may be mounted in a fluid-filled bag mounted on a movable arm (not shown) that may be placed in contact with a patient, such as that described in U.S. Pat. No. 5,526,814, the disclosure of which is expressly incorporated herein by reference.

In addition, an imaging device (not shown) may be used for monitoring the use of the system 10 during treatment of a patient. For example, the system 10 may be placed within a magnetic resonance imaging (MRI) device, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

Returning to FIG. 3, during use, a patient 44 may lie on the table 36 with water, ultrasonic conducting gel, and the like applied between the patient 44 and the bag or membrane 42, thereby acoustically coupling the patient 44 to the transducer 12. The transducer 12 may be focused towards a target tissue region 46 within a tissue structure, such as a cancerous or benign tumor. The transducer 12 may be activated by supplying a set of drive signals $S_{EMIT}$ at a discrete frequency to the transducer 12 to focus the emitted ultrasonic energy $U_{EMIT}$ at the target tissue region 46. During the course of the sonication, the frequency of the drive signals $S_{EMIT}$ may remain constant, or may be changed periodically, as described in the '159 application. The transducer 12 may be activated for sufficient time to substantially necrose the target tissue region 46, e.g., between about 5–20 seconds, and more preferably about 10 seconds or more.

The transducer 12 may be deactivated, for example, for sufficient time to allow heat absorbed by the patient's tissue to dissipate, e.g., between about 45–90 seconds, and more preferably about 60 seconds or more. The transducer 12 may then be focused on another target tissue region (not shown), for example, adjacent to the target tissue region 46, and the process repeated until the entire tissue structure is ablated.

Figure 4:
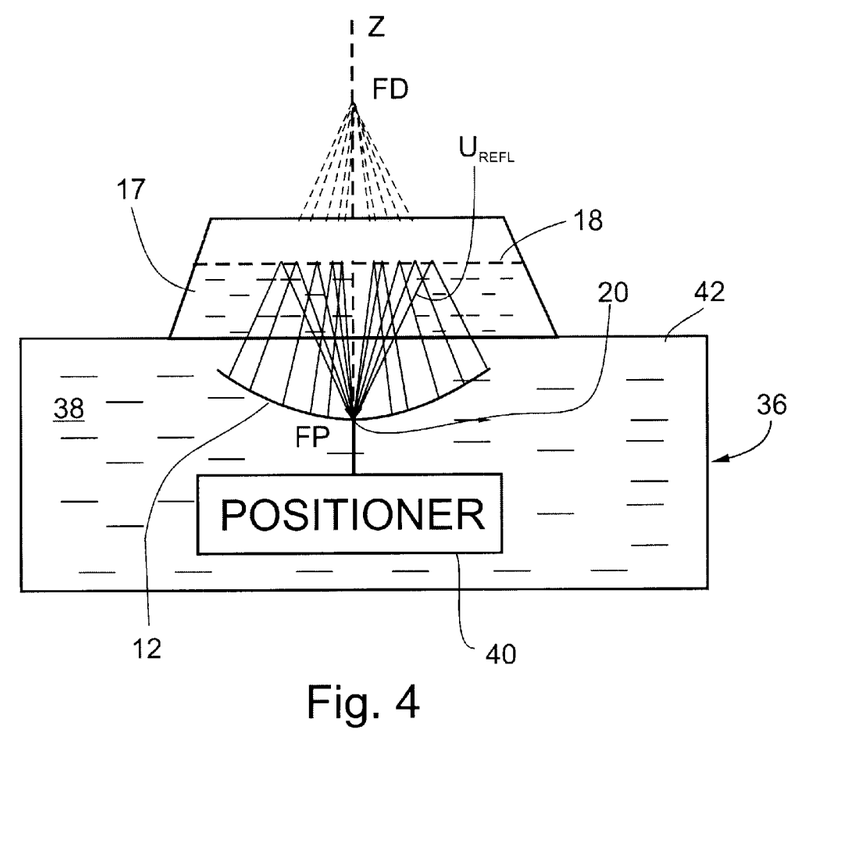
FIG. 4 is a schematic side view of a test setup for testing the ultrasound system of FIG. 1.

Turning to FIGS. 1 and 4, before performing a therapeutic procedure, the system 10 may be tested for failures and/or calibrated to ensure that the components of the system 10, such as the transducer elements 30 or the drive circuitry 14, are performing properly. For this purpose, the system 10 may include an acoustic reflector 18 (shown in FIG. 4) for reflecting ultrasonic energy $U_{REFL}$ emitted by the transducer elements 30, an ultrasound sensing element 20 for sensing the reflected ultrasonic energy $U_{REFL}$, and processing circuitry 22 for measuring the reflected ultrasonic energy $U_{REFL}$. As will be described in further detail below, the controller 16 may quantify the acoustic behavior, i.e., the performance, of the system 10 based upon the reflected ultrasonic energy $U_{REFL}$ measured by the processing circuitry 22. For example, the controller may incrementally test system channels, e.g., test the performance of individual transducer elements 30, and/or may simultaneously test groups of system channels, e.g., test a plurality of transducer elements 30 for cross-coupling or cross-talk. For the purposes of this specification, a system channel includes either or both of an electronic channel between an oscillator (not shown) of the driver circuitry 14 and a respective transducer element 30, and an acoustic channel between the respective transducer element 30 and the sensing element 20.

Referring to FIG. 4, the table 36 may provide the necessary environment for testing the system channels. As is done in actual use, the chamber 38 of the table 36 is filled with water or other acoustically transmitting fluid, and enclosed at the top with the membrane 42. A vessel 17 with an acoustically transparent bottom may be placed over the membrane 42, and partially filled with water or other acoustically transmitting fluid, thereby creating an acoustic reflector 18 at the interface between the water and the air within the vessel 17. Due to the density differences between air and water, emitted ultrasonic energy $U_{EMIT}$ incident on the acoustic reflector 18 is reflected back towards the transmitting transducer 12. In this sense, the acoustic reflector 18 may be characterized as an "air mirror," which is planar by virtue of the self-leveling characteristic of the water. The acoustic reflector 18 is preferably located half-way between the transducer 12 and the geometric focal point FP of the transducer 12.

Preferably, the relative tilt angle between the transducer 12 and the acoustic reflector 18 is substantially zero (e.g., less than about 0.1 degree), i.e., the plane of the acoustic reflector 18 is substantially perpendicular to the "z" axis of the transducer 12. If the positioner 40 has two degrees of freedom as explained above, the positioner 40 may be employed to properly align the transducer 12 and the acoustic reflector 18 in this configuration, thereby ensuring that the reflected ultrasonic energy $U_{REFL}$ is directed at the sensing element 20. Because of the possibility of the transducer 12 and the acoustic reflector 18 being out of alignment with one another, an estimation algorithm may be used to estimate any deviation of the reflector 18 and/or transducer 12 from a zero relative tilt angle. The relative tilt angle is a function of two parameters, namely the two tilt angles of the transducer 12 in two planes perpendicular to the reflector plane of the reflector 20, e.g., the orthogonal tilt angles that the z-axis of the transducer 12 deviates from being normal to the reflector surface of the reflector 20. If the tilt angles are not substantially zero, additional deviations in phase may be introduced into the reflected ultrasonic energy $U_{REFL}$. These additional deviations are simply a function of geometry, i.e., of the tilt angles, which may be estimated by performing a two-parameter least squares fit on a large number of measured phase deviations, e.g., using the reflected ultrasonic energy $U_{REFL}$ received for all of the transducer elements 30. The least squares fit calculation may yield an approximation of the two tilt angles and the phase deviations caused by this misalignment. The calculated phase deviations from the estimation algorithm may be subtracted from the measured phase deviations to yield residual phase deviations that may be used to evaluate the performance of the system, as described further below.

The geometry of the acoustic reflector 18 provides a well-defined and predictable acoustic reflection. In this manner, the ultrasonic reflection characteristics of the acoustic reflector 18 may be more easily modeled, and thus, the expected characteristics of the reflected ultrasonic energy $U_{REFL}$ may be more easily determined, as will be discussed in further detail below.

The acoustic reflector 18 intersects the z axis of the transducer 12 intermediate to and preferably half-way between the geometric focal point FP and the center of the transducer 12. Preferably, the plane of the acoustic reflector 18 is substantially perpendicular to the z axis of the transducer 12, as explained above. With the reflector 18 at the half-way point, reflected ultrasonic energy $U_{REFL}$ is directed to a point, specifically to the center of the transducer 12. This point represents the virtual geometric focal point $FP_V$ of the transducer 12. Thus, if one-hundred percent of the emitted ultrasonic energy $U_{EMIT}$ incident on the acoustic reflector 18 is reflected therefrom, the characteristics of the emitted ultrasonic energy $U_{EMIT}$, e.g., amplitude and phase, that would have been exhibited at the actual geometric focal point FP of the transducer 12, are instead exhibited at the virtual focal point $FP_V$ in the reflected ultrasonic energy $U_{REFL}$. Even if the wave amplitude suffers some decrease at the acoustic reflector 18, the relative phases of the ultrasound waves exhibited at the virtual geometric focal point are still the same as they would be at the actual geometric focal point. As will be described in further detail below, this arrangement simplifies the analysis that the controller 16 performs in quantifying the acoustic behavior of the system 10.

Referring back to FIG. 1, the sensing element 20 (or alternatively, a plurality of sensing elements) is located at the virtual geometric focal point $FP_V$, i.e., at the center of the transducer 12. The sensing element 20 senses the reflected ultrasonic energy $U_{REFL}$, transforming it into an electrical signal $S_{REFL}$. The processing circuitry 22 is coupled to the sensing element 20 for generally measuring parameters related to the ultrasonic energy, preferably "gain" and "delay." Gain is the ratio of the amplitude of the emitted ultrasonic energy $U_{EMIT}$ to the amplitude of the reflected ultrasonic energy $U_{REFL}$. Delay may be the actual time delay for ultrasonic energy emitted by a transducer element to reach the sensing element, for example, if the ultrasonic energy is emitted in relatively short pulses. More preferably, for a sinusoidal signal, delay is generally defined in terms of "phase shift" between the two sinusoidal signals, i.e., between the signals defining the emitted and received ultrasonic energy.

Specifically, the processing circuitry 22 may be coupled to the output of the sensing element 20 to measure the amplitude and phase of the electrical signal $S_{REFL}$. To provide a reference for the measured amplitude and phase, the processing circuitry 22 may also be coupled to an output of the driver circuitry 14 to measure the amplitude and phase of a sampled electrical drive signal $S_{EMIT1}$. The sampled drive signal $S_{EMIT1}$ is sensed from and is proportional to the electrical drive signal $S_{EMIT}$. To account for any errors in the electronic channels, the processing circuitry 22 is preferably coupled to the source of the sampled drive signal $S_{EMIT1}$, and in particular, the output of the oscillator (not shown) within the driver circuitry 14.

Thus, the processing circuitry 22 compares the amplitude and phase of the received electrical signal $S_{REFL}$ to the amplitude and phase of the sampled drive signal $S_{EMIT1}$, outputting a digital signal $S_A$ indicative of the amplitude and/or phase of the reflected ultrasonic energy $U_{REFL}$. If the drive signal $S_{EMIT}$ is sinusoidal, the gain and phase shift between the received ultrasonic energy $U_{REFL}$ and the emitted ultrasonic energy $U_{EMIT}$ may be easily derived from the amplitude and phase indicated by the digital signal $S_A$.

The controller 16 is coupled to the output of the processing circuitry 22 to receive the digital signal $S_A$, and thus determine the gain and phase shift between the sensed reflected ultrasonic energy $U_{REFL}$ and the emitted ultrasonic energy $U_{EMIT}$. The controller 16 compares this gain and phase shift to an expected gain and phase shift, which may be obtained from an acoustic model of the system 10 stored within the controller 16. The acoustic model contains information indicating for each excitation of a transducer element 30, or alternatively, for various sets of transducer elements 30, the expected gain and phase shift of the resulting reflected ultrasonic energy $U_{REFL}$ incident at the virtual focal point $FP_V$.

In the illustrated embodiment, this acoustic modeling is made simple by the fact that the reflective characteristics of the acoustic reflector 18 are predictable, as well as the fact that the positional relationship between the acoustic reflector 18 and the transducer 12 produces a virtual)focal point $FP_V$, at which the sensing element 20 is advantageously located. That is, the incident acoustic paths from all of the transducer elements 30 on the transducer 12 to the acoustic reflector 18 and the reflected acoustic paths back to the virtual focal point $FP_V$ are substantially equal (as depicted in FIG. 4). Thus, the gain and phase shift of the received reflected ultrasonic energy $U_{REFL}$ is expected to be uniform regardless of the transducer element 30 from which the ultrasonic energy is emitted. Such an arrangement obviates the need to make off-boresight calculations, which may otherwise be required if measurements of the reflected ultrasonic energy $U_{REFL}$ are taken at locations other than the focal point FP or virtual focal point $FP_V$. Of course, the reflected ultrasonic energy $U_{REFL}$ may be measured from any location not subject to substantial interference, without straying from the principles of the present invention, although this may require additional calculations to adjust for multipath and/or other off-boresight considerations.

Any differences between the measured and expected gain and phase shift represent an error within the system 10. The controller 16 may analyze this error information, and based on this analysis, either declare a system failure, or calibrate the system 10.

The controller 16 may test each system channel in this manner by conditioning the driver circuitry 14 to sequentially excite the transducer elements 30. Thus, for each excitation of a transducer element 30, the processing circuitry 22 obtains the gain and phase shift of the corresponding reflected ultrasonic energy $U_{REFL}$. For example, for fifty-four transducer elements 30, and thus fifty-four system channels, the processing circuitry 22 may obtain fifty-four sets of gain and phase shift data. The controller 16 then compares the sets of gain and phase shift data to corresponding sets of expected gain and phase shift data to obtain the error data for each of the system channels. If an error within one or more system channels is too severe, the controller 16 may declare a system failure. In the alternative, or in conjunction with the failure declaration function, the controller 16 may use the error data to make adjustments to the system 10, thereby compensating for any errors within the system channels, and consequently calibrating the system 10.

In the alternative, or in conjunction with the testing of individual system channels, the controller 16 may also test groups of system channels, e.g., the system channels corresponding to two or more individual transducer elements 30, to verify that there is no cross-coupling between the transducer elements 30 in the groups. The controller 16 conditions the driver circuitry 14 to excite the selected group of transducer elements 30, such as a neighboring pair of transducer elements 30. The processing circuitry 22 obtains the gain and phase shift of the corresponding reflected ultrasonic energy $U_{REFL}$. Linear superposition may be employed to determine the relationship of the reflected ultrasonic energy $U_{REFL}$ to the emitted ultrasonic energy $U_{EMIT}$. The controller 16 compares this gain and phase shift data to the expected gain and phase shift data to obtain the error data, and ultimately the extent of cross-coupling. Again, the controller 16 may declare a system failure, or calibrate the system 10, based on this error data. Once the error data has been confirmed to be negligible and/or the system calibrated to adjust for any errors, the subsequent acoustic beams of ultrasonic energy emitted by the transducer 12 may be predicted with a high confidence.

Figure 5:
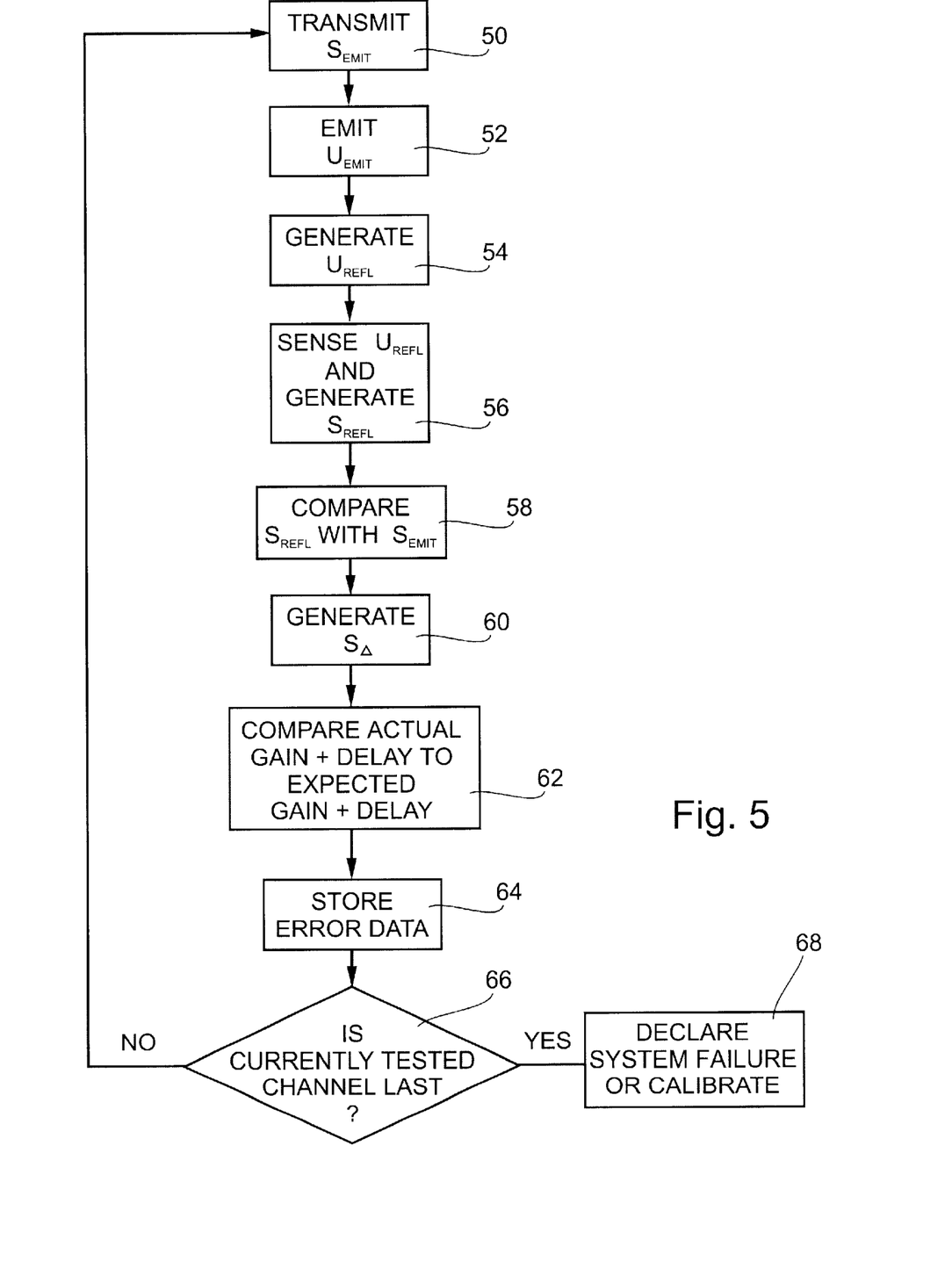
FIG. 5 is a flow diagram of a preferred method of testing the ultrasound system of FIG. 1.

Referring to FIG. 5, operation of the system 10 during the individual testing of the system channels is shown. At step 50, the controller 16 conditions the driver circuitry 14 to transmit a drive signal $S_{EMIT}$ to a specified transducer element 30. In response, the excited transducer element 30 emits an ultrasonic signal $U_{EMIT}$ towards the acoustic reflector 18 at step 52. At step 54, a reflected ultrasonic signal $U_{REFL}$ is generated by reflecting the emitted ultrasonic signal $U_{EMIT}$ from the acoustic reflector 18 back towards the sensing element 20. The sensing element 20, at step 56, senses the reflected ultrasonic signal $U_{REFL}$, outputting a corresponding electrical signal $S_{REFL}$.

At step 58, the processing circuitry 22 obtains the gain and phase shift of the reflected ultrasonic signal $U_{REFL}$ by comparing the amplitude and phase of the electrical signal $S_{REFL}$ output from the sensing element 20 to the amplitude and phase of the sample of the corresponding electrical signal $S_{EMIT1}$ output from the oscillator of the driver circuitry 14. Alternatively, the actual delay may be compared if non-sinusoidal, e.g., pulsed signals, are used. At step 60, the processing circuitry 22 then outputs an electrical signal $S_A$ indicative of the gain and phase shift of the received ultrasonic signal $U_{REFL}$.

At step 62, the controller 16 obtains the actual gain and/or phase shift from the digital signal $S_A$, comparing these parameters to the expected gain and/or phase shift. At step 64, the controller 16 then stores the difference in memory as error information. At step 66, the controller 16 then determines whether the currently tested system channel (or transducer element 30) is the last system channel to be tested. If not, the system 10 returns to step 50 where the testing of another channel will be initiated by transmitting a drive signal $S_{EMIT}$ to another transducer element 30. If the currently tested system channel is the last channel to be tested, the system 10 obtains the stored error information (from all tested channels) from memory, and either declares a system failure, or calibrates the system 10 accordingly. In a preferred method, the process for testing each system channel lasts about one hundred fifty microseconds, with each transducer element 30 being excited for a period of about twenty microseconds.

Operation of the system 10 during the testing of groups of system channel is similar to the individual testing of the system channels described with respect to FIG. 5, with the exception that the controller 16 conditions the driver circuitry 14 to transmit a set of drive signals $S_{EMIT}$ rather than a single drive signal $S_{EMIT}$, for example, to a specified set of transducer elements 30, such as to a neighboring pair of transducer elements 30, at step 50. In response, the excited transducer elements 30 in the set simultaneously emit ultrasonic signals $U_{EMIT}$ towards the acoustic reflector 18 at step 52. Additionally, when determining the gain and phase shift of the sensed reflected ultrasonic energy $S_{REFL}$ at step 58, the sampled electrical signals $S_{EMIT1}$ output from the oscillator of the driver circuitry 14 are combined prior to comparison with the electrical signal $S_{REFL}$ output from the sensing element 20. The resulting comparison preferably complies with linear superposition of the set, otherwise an error is indicated.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A method for testing a focused ultrasound transducer, comprising:

locating an acoustic reflector in a position to receive an ultrasonic signal transmitted by the transducer;

transmitting an emitted ultrasonic signal from the transducer towards the acoustic reflector;

receiving a reflected ultrasonic signal reflected off of the acoustic reflector;

evaluating the transducer performance based upon the received reflected ultrasonic signal; and using an estimation algorithm to estimate any deviation in alignment between the acoustic reflector and transducer;

wherein the step of evaluating the transducer performance comprises adjusting the transducer performance evaluation based upon the estimated deviation to correct for any misalignment between the acoustic reflector and the transducer.

2. The method of claim 1, wherein the estimation algorithm comprises performing a least squares fit on measured phase deviations from a plurality of transducer elements comprising the transducer to yield an approximation of any deviation in alignment between the acoustic reflector and the transducer.

3. A method for testing a focused ultrasound transducer, comprising:

locating an acoustic reflector in a position to receive an ultrasonic signal transmitted by the transducer;

transmitting an emitted ultrasonic signal from the transducer towards the acoustic reflector;

receiving a reflected ultrasonic signal reflected off of the acoustic reflector; and evaluating the transducer performance based upon the received reflected ultrasonic signal;

wherein the transducer has a geometric focal point, and wherein the acoustic reflector comprises a planar reflector located half-way between the transducer and the geometric focal point.

4. The method of claim 3, wherein the reflected ultrasonic energy is received by a sensing element at a center of the transducer.

5. The method of claim 3, further comprising calibrating individual transducer elements of the transducer based on the evaluated transducer performance.

6. The method of claim 3, wherein the transducer includes a plurality of transducer elements, and wherein the step of transmitting an emitted ultrasonic signal comprises simultaneously transmitting one or more ultrasonic signals from a set of the plurality of the transducer elements towards the acoustic reflector.

7. The method of claim 6, wherein the step of evaluating the transducer performance comprises:

obtaining a received ultrasonic characteristic from the received ultrasonic signal; and comparing the received ultrasonic characteristic with a linear superposition of a like ultrasonic characteristic of the one or more emitted ultrasonic signals.

8. The method of claim 6, wherein the step of evaluating the transducer performance comprises determining a gain and phase shift of the received ultrasonic signal by comparing the amplitude and phase of the received ultrasonic signal with corresponding amplitudes and phases of the one or more emitted ultrasonic signals.

9. An ultrasound system, comprising:

a spherical cap transducer array including one or more transducer elements, the transducer elements configured for transmitting an emitted ultrasonic signal;

an acoustic reflector positioned to reflect at least a portion of an emitted ultrasonic signal transmitted by one or more of the transducer elements;

a sensing element located at a center of the spherical cap transducer array to receive a received ultrasonic signal comprising at least a portion of the ultrasonic signal reflected off of the acoustic reflector;

processing circuitry coupled to the sensing element for measuring an actual characteristic of the received ultrasonic signal; and a controller coupled to the processing circuitry for comparing the actual characteristic of the received ultrasonic signal to an expected characteristic of the received ultrasonic signal;

wherein the acoustic reflector is positioned half-way between the spherical cap transducer array and its geometric focal point.

10. An ultrasound system, comprising:
- a transducer including one or more transducer elements, the transducer elements configured for transmitting an emitted ultrasonic signal;
- a planar acoustic reflector positioned to reflect at least a portion of an emitted ultrasonic signal transmitted by one or more of the transducer elements;
- a sensing element positioned to receive a received ultrasonic signal comprising at least a portion of the ultrasonic signal reflected off of the acoustic reflector;
- processing circuitry coupled to the sensing element for measuring an actual characteristic of the received ultrasonic signal; and
- a controller coupled to the processing circuitry for comparing the actual characteristic of the received ultrasonic signal to an expected characteristic of the received ultrasonic signal,
- wherein the transducer comprises a plurality of transducer elements and wherein the sensing element is positioned for receiving at least a portion of an ultrasonic signal reflected off of the acoustic reflector from each of the transducer elements.

11. The ultrasound system of claim 10, wherein the transducer comprises a spherical cap transducer array, and wherein the sensing element is located at a center of the spherical cap transducer array.

12. The ultrasound system of claim 10, wherein the processing circuitry is configured for measuring the actual characteristic of the received ultrasonic energy by comparing a characteristic of the received ultrasonic signal with a corresponding characteristic of the emitted ultrasonic signal.

13. The ultrasound system of claim 12, wherein the processing circuitry is further configured for comparing at least one of phase and amplitude of the received ultrasonic signal and the emitted ultrasonic signal.

14. A method for testing a focused ultrasound transducer, comprising:
- transmitting an ultrasonic signal from a transducer element of a transducer array towards an acoustic reflector;
- receiving the ultrasonic signal reflected off of the acoustic reflector from the transducer element at a sensing element that is different than the transducer element; and
- evaluating performance of the transducer array based upon the ultrasonic signal received by the sensing element,
- wherein the transducer array has a geometric focal point, and wherein the acoustic reflector comprises a planar reflector located between the transducer array and the geometric focal point.

15. The method of claim 14, wherein the transducer array comprises a plurality of transducer elements, and wherein the sensing element receives ultrasonic signals reflected off of the acoustic reflector from respective transducer elements.

16. The method of claim 14, wherein the performance is evaluated by comparing an actual characteristic of the ultrasonic signal received by the sensing element to an expected characteristic of the ultrasonic signal received by the sensing element.

17. The method of claim 16, wherein the actual characteristic comprises a difference between a component of an electrical signal generated by a sensing element that receives the ultrasonic signal, and a corresponding component of an electrical signal used to generate the ultrasonic signal.

18. The method of claim 16, wherein the actual characteristic is a gain comparing the amplitude of the ultrasonic signal received by the sensing element to the amplitude of the ultrasonic signal emitted by the transducer element.

19. The method of claim 16, wherein the actual characteristic is a delay between the ultrasonic signal received by the sensing element and the ultrasonic signal emitted by the transducer element.

20. The method of claim 16, wherein the ultrasonic signal emitted by the transducer element comprises a sinusoidal wave, and wherein the actual characteristic is a phase shift between the ultrasonic signal received by the sensing element and the ultrasonic signal emitted by the transducer element.

* * * * *